(12) United States Patent
Knip

(10) Patent No.: US 11,871,722 B2
(45) Date of Patent: Jan. 16, 2024

(54) MILKING SYSTEM WITH DETECTION SYSTEM

(71) Applicant: LELY PATENT N.V., Maassluis (NL)

(72) Inventor: Abram Christiaan Knip, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 525 days.

(21) Appl. No.: 17/273,770

(22) PCT Filed: Sep. 19, 2019

(86) PCT No.: PCT/NL2019/050618
§ 371 (c)(1),
(2) Date: Mar. 5, 2021

(87) PCT Pub. No.: WO2020/067880
PCT Pub. Date: Apr. 2, 2020

(65) Prior Publication Data
US 2021/0315181 A1    Oct. 14, 2021

(30) Foreign Application Priority Data

Sep. 24, 2018   (NL) ...................................... 2021692

(51) Int. Cl.
*G01N 33/04* (2006.01)
*A01J 5/013* (2006.01)
*G01N 1/20* (2006.01)

(52) U.S. Cl.
CPC .......... *A01J 5/0131* (2013.01); *G01N 1/2035* (2013.01); *G01N 33/04* (2013.01)

(58) Field of Classification Search
CPC ....... A01J 5/0131; G01N 1/10; G01N 1/2035; G01N 21/8483; G01N 2021/7773; G01N 2021/7786; G01N 33/05; G01N 35/00009
See application file for complete search history.

(56) References Cited

U.S. PATENT DOCUMENTS 3,526,480 A    9/1970  Findl et al.
5,077,010 A *  12/1991 Ishizaka ........... G01N 35/00009
                                                           422/62

(Continued)

FOREIGN PATENT DOCUMENTS

CN           1631120 A      6/2005
WO      WO 02/069697 A1    9/2002

(Continued)

OTHER PUBLICATIONS

Mao, "Engineering Practice Training Manual for Food Excellence Engineers," China Ocean University Press, Jul. 31, 2017, 38 pages total.

(Continued)

*Primary Examiner* — Alexander A Mercado
(74) *Attorney, Agent, or Firm* — Birch, Stewart, Kolasch & Birch, LLP

(57) ABSTRACT

A robotic milking system includes a milking control, a milk line, and a sampling and analysis device for the milk, wherein the milking control controls the robotic milking device based on the analysis of the milk sample. The sampling and analysis device includes a control unit, a tape reel with a tape with reagent pads that detect the presence of a substance in the sample, a tape mover, a dosing device to provide a sample onto a reagent pad, a camera to image of the reagent pad with said sample, and to analyse the images to indicate a presence or concentration of said substance. The lengthwise consecutive substantially rectangular reagent pads are separated by a hydrophobic line, and the control unit recognises said line in the image and determines a position thereof. The control unit controls the tape mover on the basis of the obtained image and line position.

20 Claims, 2 Drawing Sheets

(56) References Cited

U.S. PATENT DOCUMENTS

Figure 1:
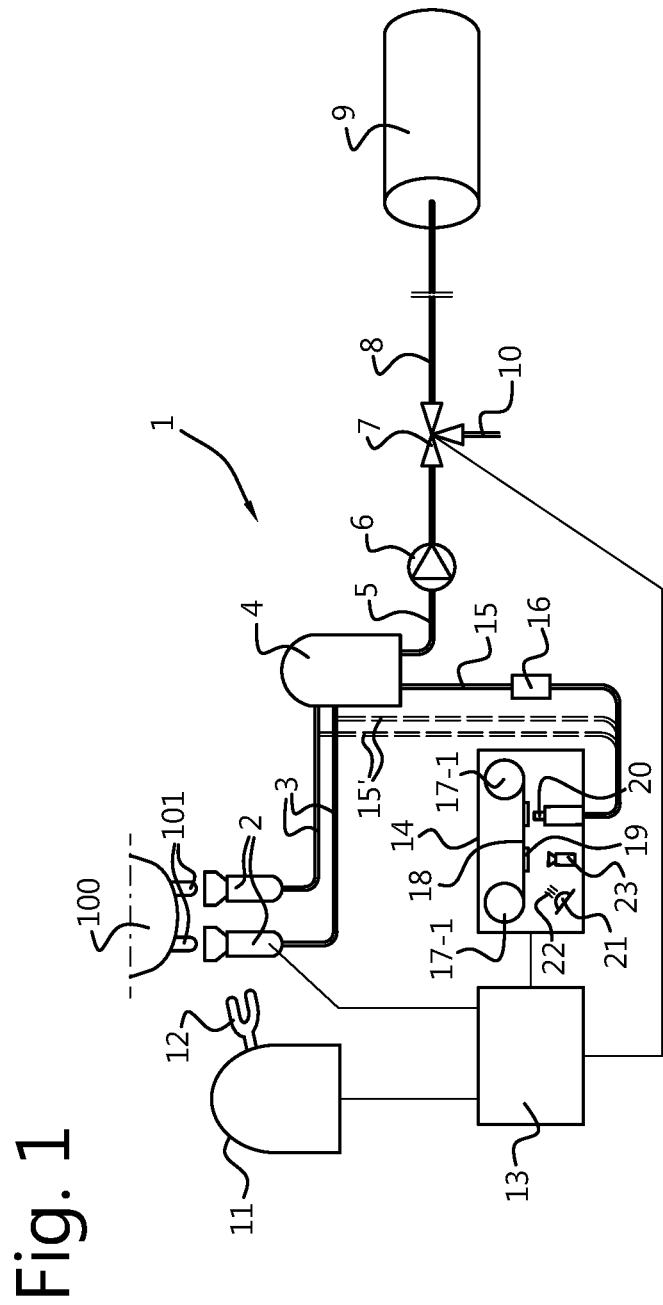

| | | | |
|---|---|---|---|
| 5,096,828 A * | 3/1992 | Ishizaka | G01N 35/00009 422/66 |
| 9,232,764 B2 * | 1/2016 | Axelson | A01J 5/0132 |
| 11,567,090 B2 * | 1/2023 | Dallerup Rasmussen | G01N 33/04 |
| 2002/0124803 A1 * | 9/2002 | Chen | A01K 1/12 119/14.08 |
| 2005/0123948 A1 | 6/2005 | Claycomb et al. | |
| 2006/0260939 A1 * | 11/2006 | Anderson | G01N 33/04 204/403.01 |
| 2007/0217950 A1 * | 9/2007 | Kramer | A61B 5/14532 422/66 |
| 2012/0145082 A1 * | 6/2012 | Van Den Berg | A01J 5/017 119/14.08 |
| 2014/0148378 A1 | 5/2014 | Lebrilla et al. | |
| 2016/0050878 A1 | 2/2016 | Pennarun | |
| 2017/0099810 A1 * | 4/2017 | Auer | A01K 11/006 |
| 2020/0000055 A1 * | 1/2020 | Mostert | A01J 5/01 |
| 2021/0185972 A1 * | 6/2021 | Gavin | A01J 5/007 |
| 2021/0195863 A1 * | 7/2021 | Gavin | G01N 1/10 |
| 2021/0259194 A1 * | 8/2021 | Dessing | A01J 5/013 |
| 2021/0308683 A1 * | 10/2021 | Gavin | G01N 35/00029 |
| 2021/0315181 A1 * | 10/2021 | Knip | G01N 1/2035 |
| 2021/0329877 A1 * | 10/2021 | Dessing | G01N 15/0612 |
| 2021/0341447 A1 * | 11/2021 | Gavin | G01N 33/04 |
| 2021/0345576 A1 * | 11/2021 | Dessing | G01N 35/00009 |

FOREIGN PATENT DOCUMENTS

| | | |
|---|---|---|
| WO | WO 2004/034063 A2 | 4/2004 |
| WO | WO 2014/162009 A2 | 10/2014 |
| WO | WO 2020/067876 A1 | 4/2020 |

OTHER PUBLICATIONS

International Search Report, issued in PCT/NL2019/050618, dated Feb. 19, 2020.
Written Opinion of the International Searching Authority, issued in PCT/NL2019/050618, dated Feb. 19, 2020.

* cited by examiner

MILKING SYSTEM WITH DETECTION SYSTEM

The present invention relates to a milking system, comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the robotic milking means on the basis of the analysis of the milk sample, wherein the sampling and analysis device comprises a control unit for controlling the sampling and analysis device, a tape reel provided with a tape with a series of reagent pads that are arranged to provide a detectable response in the presence of at least one substance in the sample, a tape mover, arranged to move the tape under control of the control device, a dosing device arranged to provide under the control of the control unit a droplet of the sample onto a reagent pad on the tape, a camera device operably connected to the control unit, and arranged to obtain at least one image of said part of the reagent supplied with said droplet of the sample, and to analyse the at least one obtained image to provide an indication of a presence or concentration of said at least one substance, wherein the reagent pads are lengthwise consecutive substantially rectangular reagent pads.

Such a milking systems are in principle known, and are capable of analysing a milk sample by means of a reagent's response to the presence or concentration of at least one substance in the milk. This may be a signal for direct use during the milking turn, or for use in a subsequent milking, such as by way of an attention signal in a database. In any case, after sampling, the system is to be made ready for a subsequent sampling. Thereto, a new reagent pad will be positioned to receive the sample drop, by moving the tape reel.

The known systems have the drawback that they are not well able to ensure a long unsupervised use of the milking system in general, and in particular the sampling and analysis device, while at the same time ensuring a correct positioning of the reagent pads, which is of course desirable to obtain a reliable and high-quality analysis result.

It is therefore an object of the invention to provide a milking system of the kind described above, in which the above problems are solved or at least mitigated.

Thereto, the present invention provides a milking system according to claim 1, in particular a milking system, comprising a robotic milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the robotic milking means on the basis of the analysis of the milk sample, wherein the sampling and analysis device comprises a control unit for controlling the sampling and analysis device, a tape reel provided with a tape with a series of reagent pads that are arranged to provide a detectable response in the presence of at least one substance in the sample, a tape mover, arranged to move the tape under control of the control device, a dosing device arranged to provide under the control of the control unit a droplet of the sample onto a reagent pad on the tape, a camera device operably connected to the control unit, and arranged to obtain at least one image of said part of the reagent supplied with said droplet of the sample, and to analyse the at least one obtained image to provide an indication of a presence or concentration of said at least one substance, wherein the reagent pads are lengthwise consecutive substantially rectangular reagent pads, that are mutually separated by a hydrophobic separator line, and wherein the control unit is arranged to recognise said separator line in the obtained images and to determine a position of said separator line in the image, and wherein the control unit is arranged to control the tape mover on the basis of the obtained images.

It was realised by the inventor that a primary advantage of a milking system with a robotic milking means is that milking may proceed without human supervision. This also requires reliable and high-quality measurements of milk quality, for example in order to fulfil legal requirements as to consumption milk quality. It is then not desirable when some additional system needs frequent human intervention, such as to change the tape reel with the reagent pads. Thus, a high number of reagent pads is desirable, however without requiring more space. This would mean that the pads need to be closer together. But that in turn requires a higher precision in positioning the pads, to prevent that two pads each receive part of a sample drop, or are each partly analysed to deliver one mixed, and thus incorrect analysis result. In addition, the reagents often contain enzymes or other biologically produced substances, which are costly to make. Therefore, providing larger pads to prevent this mixing up of samples or analysis results is neither desirable.

In order to unite the above described desires of a long and uninterrupted use of the milking system while still having a reliable analysis result, the inventors found to use hydrophobic separator lines to delimit the reagent pads. A hydrophobic separator line can be made very narrow, which allows the pads to be very close without influencing each other. This means that more pads can be positioned on a tape of a certain length. In addition, the separator line is not only narrow, but also very sharply defined and may easily be made rather dark. In most cases this will contrast sharply with the often much brighter/whiter colour of the reagent pads. Both these properties help in accurately determining the position of the separator lines, and hence the position of the reagent pads, by means of optical object recognition in the images. This allows a longer uninterrupted sampling time, while still having a precise position control of the pads, and thus a reliable and accurate analysis of the samples.

It is remarked here that the analysis result might be used in-line, for example if foremilk is analysed and the analysis result leads to the subsequently milked milk being separated, or it might be used for future milkings. Then the analysis result, or an action to be based on this result, is stored in a database. The analysis result may either be useful for control of the milking of the relevant animal, or possibly of a group to which the animal belongs, such as heifers or recently calved cows, or of the herd as a whole. The result may be used by itself, or as part of a series of measurements, such as a time-averaged value. It is furthermore remarked that "lengthwise consecutive" means that the reagent pads are consecutive when seen in the longitudinal direction of the tape. Herein, it is possible that there are two or more series of lengthwise consecutive reagent pads, but in each case, i.e. per series, the invention relates to the pads that are arranged consecutively in the longitudinal direction of the tape.

According to the invention, the control unit is arranged to recognise said hydrophobic separator line in the obtained images and to determine a position of said separator line in the image, and to control the tape mover on the basis of the obtained images. This control may be brought about by means of feedback to the tape mover. Herein, the camera device obtains images repeatedly, which images are subsequently processed in-line. The position of the laser ablation line is determined and followed while the tape is moving. The tape mover is stopped if the separator line is in position, or at least the tape mover will be controlled such that the end result is that the separator line is in the intended position.

Particular embodiments and advantages of the invention are described in the dependent claims and the now following part of the description.

In embodiments, the hydrophobic separator line is or comprises a laser ablation line. Since a laser ablation line can be made very narrow, such as one or a few tenths of a millimeter, which allows the pads to be very close without influencing each other. Also, such a laser ablation line can be made very quickly, and is very effective as a hydrophobic barrier blocking flow of watery liquids from pad to pad, as has been described in our concurrently filed co-pending US patent application 'Method of producing a reagent tape, reagent tape and milking device with a milk sampling device therewith', application No. U.S. 62/735,212

In embodiments, the hydrophobic separator line is or comprises a hydrophobic coating line. Such coating lines have also been described in the abovementioned US patent application, and have more or less the same advantages. Advantageously, they can easily be given a colour that contrasts well with the reagent material, so image quality and positioning accuracy may even be further improved, in particular for dark reagent materials.

In embodiments, the control unit is arranged to control the tape mover to move the tape over such a distance that another of said hydrophobic separator lines, in particular a neighbouring hydrophobic separator line, is moved into said determined position. In cases wherein there is a single hydrophobic separator line between the reagent pads, this laser line determines the exact border between two pads. Therefore, positioning of the reagent pads comes down to positioning the hydrophobic separator line. And shifting the tape one pad, to bring the next reagent pad into a position for receiving the sample droplet, shifting the tape over such a distance that the very next hydrophobic separator line as recognised in the (repeatedly determined) image comes in the position of the previous hydrophobic separator line. Herein, it is noted that object recognition in images is in and by itself a well-known technology, which the skilled person can put to use in the present invention without any specific difficulties. Herein, a line is one of the simplest objects to recognise, which in turn makes the invention simple and straightforward to implement.

In embodiments, the control unit is arranged to control the tape mover to move the tape over such a distance that the Nth subsequent hydrophobic separator line, is moved into said determined position, the distance being substantially equal to N times a centre-to-centre distance between lengthwise neighbouring pads, where N=2, 3, . . . . Said distance is substantially equal to a centre-to-centre distance between lengthwise neighbouring pads, or some multiple thereof in the case of skipping one or more pads. This situation, in which one or more reagent pads are skipped, may be encountered when it is decided that those one or more to-be-skipped reagent pads are not usable, for example because they have been affected by humidity, some other contaminent, or any other reason. This may be brought about when for example the analysis device is opened for maintenance, or when the reel is installed. In such cases, the reagent pads closest to an exit opening of the tape reel might have been exposed to too much humidity, ambient air or the like, and it is then decided to unwind the tape for a number of pads. This may be compared to unwinding a roll of photographic film for a number of "blank" exposures. In such a case, skipping one or more reagent pads comes down to positioning not the next laser line into position, but the "1+one or more"-th laser line.

In embodiments, the camera is positioned such that it has a field of view that contains a plurality of pads. This allows a more reliable positioning of the pads. Although each line will appear smaller in the image, and it will in principle will be more difficult to determine its position, this may be outdone by the circumstance that more consecutive lines should be, and will be, detectable in the image. Knowing that shifting the tape over a certain distance will shift a new laser line into a position of a laser line as visible in the previous position helps in case a laser line would be difficult or even impossible to detect. For example, if a laser line would be deformed from the expected straight line, it may not be detected, or less precise. If some dirt would partially or wholly cover the hydrophobic separator line, it may not be detectable, and so on. In all these cases, having the hydrophobic separator line(s) of one or more additional reagent pads in the image helps in positioning the tape correctly and more in particular reliably.

An additional advantage to be mentioned here is that having more reagent pads in the image allows a longer reaction time for the reaction of the sample in the reagent pad. Subsequent milkings may follow each other after only a short time, sometimes as short as a few minutes. Sometimes this is too short for a reliable analysis before the reagent pad would be shifted out of the field of view of the camera device. Now having more pads in view may at least double that time. In turn, in case imaging of one reagent only would already suffice, then this measure allows to have less reagent in the pad while still ensuring a reliable reaction, because only the time-scale would be stretched.

In embodiments, the reagent pads are mutually separated by a set of at least two, and preferably two, mutually parallel laser ablation lines. Having such a double laser line helps in further delimiting the reagent pads, by having a double barrier for fluid, and it allows to seal with a sealing means onto the tape without affecting the reagent pads and without forming a liquid bridge via that very sealing means. It also helps in more reliably determining the position of the reagent pads. It is noted that in the case of the hydrophobic separator lines being a coating line, it would suffice to make the line itself wider, which is less easy and efficient in the case of a laser line.

The above described situation of multiple reagent pads in the field of view also used the presence of multiple laser ablation lines, but the present measure allows to have only slightly more than the one reagent pad in the image. Thereby, the lines are larger in the image and can be discerned more clearly, and their positions be determined more clearly. In addition, when one of the lines is not very clear in the image, while the other is, its presence and detection will still help in correctly positioning the reagent pad. Needless to say, moving a next reagent pad into position in these embodiments will require the moving of a set of laser ablation lines to the position of the previous set of laser lines instead of moving just one laser line into that previous position.

Figure 2:
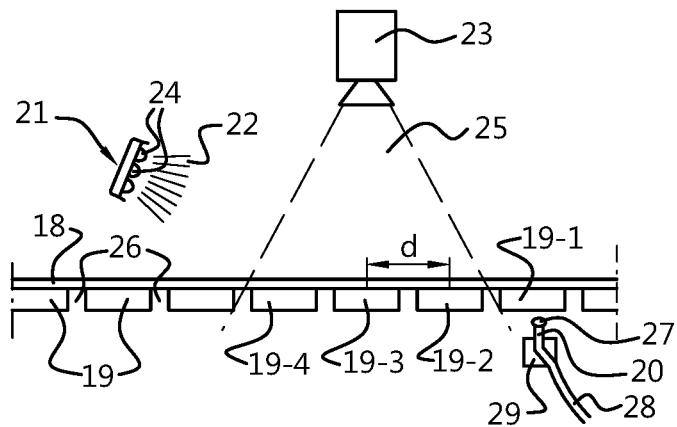
Figure 3:
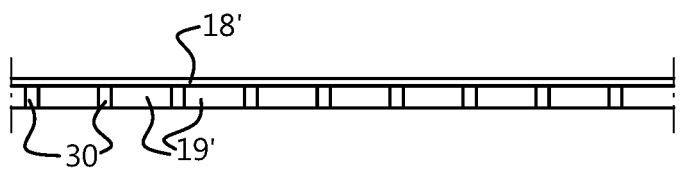
Figure 4:
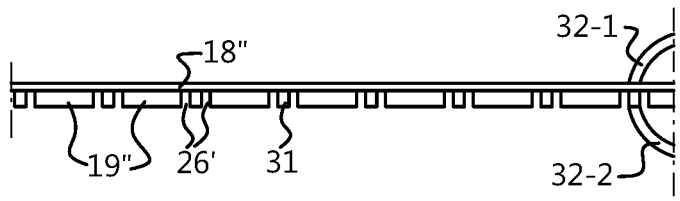

The invention will now be elucidated by way of a number of exemplary embodiments and the drawings, in which FIG. 1 shows a diagrammatic representation of a milking system according to the present invention;

FIG. 2 diagrammatically shows a detail of a milking system according to the invention; and FIGS. 3 and 4 diagrammatically show a yet smaller detail of other embodiments of the invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16. the sampling unit 14 comprises a supply reel 17-1 and a collecting reel 17-2 for a tape 18 with reagent pads 19. A nozzle device for sample droplets is denoted by 20, a light source 21 emits light 22, and a camera is denoted by 23.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be OK, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 15. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on.

A sampling unit 14 is very generally shown further, in that it here contains a supply reel 17-1 and a collecting reel 17-2, between which a tape 18 is wound down by means of non-shown tape mover means, such as a cassette deck motor or stepper motor. The tape 18 carries reagent pads 19 that contain reagent that gives a detectable response in the presence of a defined substance, often the intensity of the response depending on the concentration of the substance brought into the reagent via the sample droplet. Such a sample droplet is delivered via the nozzle 20. A light source 21 then shines light 22 onto the reagent pad 19, and a camera 23 observes the response, if any, in the reagent pad. The light source 21 may be any suitable light source, such as one or more LEDs, and the emitted light 22 may be visible light, UV(A) radiation, (near) infrared, and so on, depending on the used reagent. Of course, the camera 23 should be adapted to detect radiation coming from the reagent pad 19. Often, this is reflected or scattered light, but it could be different radiation, such as fluorescence radiation. In any case, details of such radiation and detection may easily be implemented by the skilled person and do not form the present invention as such.

It is remarked here that the camera 23 and the light source 21 are shown below the tape 18 with the reagent pads 19. In practice, it may also occur, and in fact often be advantageous, if the camera 23 and the light source 21 are positioned above the tape 18. This allows the camera to image the reagent pad to which the sample droplet is supplied without advancing the tape, i.e. immediately. In addition, there is no risk of any liquid, or dirt, falling from the reagent pad to the camera and/or light source. Moreover, in general, it is advantageous if the camera 23 and/or the light source 21 are positioned outside the sampling unit 14, or rather outside a housing of the sampling unit. The camera and the light source are still functional parts of the sampling unit as a whole, but the former two parts are positioned outside a housing with the tape (reels) and the supply nozzle 20.

FIG. 2 diagrammatically shows a detail of a milking system according to the invention. Herein, similar parts are denoted by the same reference numerals. The present embodiment shows a tape 18 with reagent pads 19, in particular first through fourth reagent pads 19-1 through 19-4. A light source 21 has three LEDs and emits light 22. The camera 23 has a field-of-view 25. Between two neighbouring reagent pads 19( . . . ) there is a laser ablation line 26. The nozzle doses a droplet 27 of a milk sample delivered by a sample supply line 28. Finally, an overflow cup to catch excessive fluid ejected by the nozzle is denoted by 29.

In this embodiment, the camera 23 is mounted above the tape 18, with the reagent pads 19( . . . ) facing down, i.e. away from the camera 23. This is advantageous in that the camera can now see the reaction in the pads without being hindered by colour already developed, or by remnants of the droplet 27 of milk sample, in case that would not yet have been fully absorbed by the respective pad. Of course, the tape 18 should be sufficiently transmissive for the radiation 22, but that does not pose any specific problems to the skilled person. Such tape 18 could e.g. be a polyester-like material. Another advantage is that any surplus sample liquid, or dust or other dirt does not fall onto or even into the camera 23 or light source 21. Note that it is actually the optical path that counts, for it is possible to position a mirror above the tape 18 and under a 45 degree angle, and have the camera 23 look into the mirror horizontally. Thus, it is not the physical position that counts, but the position of the camera as seen by the tape 18 and pads 19( . . . ). Such mirror set-up may be advantageous if space is at a premium, for it is more compact.

In the embodiment shown, the nozzle 20 receives milk, or some other liquid sample, from the sample supply line 28, as dosed by a non-shown dosing or metering means. Hereby, a droplet 27 is formed, that is applied to the reagent pad 19-1. At the same time, there are three other reagent pads, viz. 19-2, 19-3 and 19-4, in the field-of-view 25 of the camera 23. These three reagent pads had been supplied with a sample droplet one, two, three samplings/milkings ago, respectively. The camera 23 was able to follow the development of the reaction in these reagent pads during the past one, two, or three milkings, although it is noted that sampling need not take place during each milking. This being able to follow the development of the response in the pad has a big advantage, in that the concentration of the reagent (enzyme or the like) need not be as high as would be required for a quick response, i.e. one that gives similar results/intensities but then during the time period of one milking. This allows thus a more efficient use of the reagents, which are often hard to produce.

In use, after the droplet 27 has been provided to the reagent pad 19-1, the tape 18 is shifted over one reagent pad length, i.e. over a distance d in the FIG. 2, the centre-to-centre distance between two consecutive reagent pads. According to the invention this is done by the camera, and its image processing/control unit, cfr. control unit 13 of FIG. 1. Thereto, the camera takes an image of the tape 18 with at least one reagent pad, here three reagent pads 19-1 . . . 3, and with the laser ablation lines 26 between each reagent pad and its neighbours. Such ablation line 26 is visible as the absence of the reagent material, i.e. mostly as a dark line in the image. In addition, laser ablation will leave a thin more or less charred surface of the reagent material. Furthermore, although the Figure shows a relatively wide ablation line 26, in practice this can be made very narrow, e.g. as narrow as about 0.1 mm. This allows a very precise positioning of the ablation lines and thus of the reagent pads.

When the system is to move the tape 18 to the next position, i.e. a shift over one centre-to-centre distance d, the tape mover (not shown here) is controlled to move the tape 18 until the position of the ablation line taken as the starting point is assumed by the very next ablation line. In the presently shown embodiment, this can be done for more than one ablation line 26, here up to four ablation lines, so that through error correction the displacement is even more reliable and accurate.

It is noted that it is also possible, and in practice often advantageous, to have the nozzle 20 apply the droplet 27 at the position of the reagent pad 19-2, i.e. already in the field-of-view 25 of the camera 23. This allows to start observing the response immediately, without first having to move the tape to bring the reagent pad with the new droplet in view of the camera 23. It is furthermore noted that it is possible to shift the tape 18 over more than one centre-tocentre distance d. For example, in case of doubt as to the quality of the very next reagent pad, it is possible to move the tape 18 over, say, two or more times the distance d. This may be compared with advancing a roll of film in an analogue camera, after loading it into the camera. The first few exposures would have been bad because of light reaching the film, and so they are advanced anyway. A similar reason in the present embodiment could be that there is a high temporary moisture load, e.g. due to exchange of a reel of tape, or maintenance or the like, so that the first few new reagent pads have a substandard quality. It is then safer to forward those few reagent pads in one go, and thereto the tape 18 is advanced over a few timed the distance d.

FIGS. 3 and 4 diagrammatically show a yet smaller detail of other embodiments of the invention. FIG. 3 shows a tape 18' with reagent pads 19' that are separated by thin layers or zones 30 of added hydrophobic barrier material. In this embodiment, no reagent material is removed from the continuous layer, but rather, separate reagent pads 19' have been created by adding a hydrophobic barrier material in a narrow zone 30 into the reagent material. thereto, a suitable material, such as a TFE polymer, paraffin or the like. This is pressed onto and into, or injected into, a continuous layer of reagent material such that hydrophobic barrier lines 30 are formed between (now) separated reagent pads 19'. These lines 30 may be formed by means of per se well-known printing techniques or the like.

FIG. 4 shows a detail of yet another embodiment, in which the reagent pads 18" are separated by a set of two laser ablation lines 26', with a narrow remaining zone 31 remaining between the two lines. Parts 32-1 and 32-2 denote two halves of a duckbill seal Having two such lines 26' provides even better liquid barrier properties, be it at the cost of a larger centre-to-centre distance, and also allows more accurate position, since the positions of both lines may be followed when advancing the tape 18'. In addition, it is now easier and more reliable to seal unused reagent pads 19" from the environment. The reagent material is often very moisture sensitive, and therefore the unused part of the tape is often kept in a cassette. For example, in FIG. 1, the supply reel 17-1 is often in a closed housing, with the tape emerging from an exit opening. Such opening may be sealed, e.g. by means of a duckbill seal 32, or other type of seal. In this way, the unused reagent pads are well protected against moisture from the environment. It is furthermore noted that, although sealing is possible on the embodiments of FIGS. 2 and 3 as well, the embodiment of FIG. 4 has the advantage that positioning accuracy may be better due to the very sharp laser ablation lines 26, while the spacing between a set of two such lines 26' is very accurately controllable, and may be made to fit the dimensions of the seal 32 used. This prevents that liquid or moisture may seep through to the unused reagent pads between the seal 32-1, 32-2 via a laser ablation line. Note that a seal would not work right above such a laser ablation line 26, because of the absence of any material there, so that liquid could flow unhindered over the surface of the seal. This is topped by the narrow zone 31 of remaining material.

The above described embodiments only serve to help explain the invention without limiting this in any way. The scope of the invention is rather determined by the appended claims.

The invention claimed is:

1. A milking system, comprising a robotic milking device with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the robotic milking device on the basis of the analysis of the milk sample, wherein the sampling and analysis device comprises:
a control unit for controlling the sampling and analysis device;
a tape reel provided with a tape with a series of reagent pads that are arranged to provide a detectable response in the presence of at least one substance in the sample;
a tape mover, arranged to move the tape under control of the control device;
a dosing device arranged to provide and under the control of the control unit a droplet of the sample onto a reagent pad on the tape; and a camera operably connected to the control unit, and arranged to obtain at least one image of said part of the reagent supplied with said droplet of the sample, and to analyse the obtained images to provide an indication of a presence or concentration of said at least one substance, wherein the reagent pads are lengthwise consecutive substantially rectangular reagent pads, that are mutually separated by a hydrophobic separator line, wherein the control unit is arranged to recognise said separator line in the at least one obtained image and to determine a position of said separator line in the image, and wherein the control unit is arranged to control the tape mover on the basis of the at least one obtained image.

2. The milking system according to claim 1, wherein the hydrophobic separator line is or comprises a laser ablation line.

3. The milking system according to claim 2, wherein the hydrophobic separator line is or comprises a hydrophobic coating line.

4. The milking system according to claim 2, wherein the control unit is arranged to control the tape mover to move the tape over such a distance that another of said separator lines is moved into said determined position.

5. The milking system according to claim 2, wherein the control unit is arranged to control the tape mover to move the tape over such a distance that the Nth subsequent separator line, is moved into said determined position, the distance being substantially equal to N times a centre-to-centre distance between lengthwise neighbouring pads, where N=2, 3, . . . .

6. The milking system according to claim 2, wherein the camera is positioned having a field of view that contains a plurality of pads.

7. The milking system according to claim 2, wherein the reagent pads are mutually separated by the separator line comprising a set of at least two mutually parallel laser ablation lines, and wherein said distance is substantially equal to a centre-to-centre distance between lengthwise neighbouring pads.

8. The milking system according to claim 1, wherein the hydrophobic separator line is or comprises a hydrophobic coating line.

9. The milking system according to claim 8, wherein the control unit is arranged to control the tape mover to move the tape over such a distance that another of said separator lines is moved into said determined position.

10. The milking system according to claim 8, wherein the control unit is arranged to control the tape mover to move the tape over such a distance that the Nth subsequent separator line, is moved into said determined position, the distance being substantially equal to N times a centre-to-centre distance between lengthwise neighbouring pads, where N=2, 3, . . . .

11. The milking system according to claim 8, wherein the camera is positioned having a field of view that contains a plurality of pads.

12. The milking system according to claim 8, wherein the reagent pads are mutually separated by the separator line comprising a set of at least two mutually parallel laser ablation lines, and wherein said distance is substantially equal to a centre-to-centre distance between lengthwise neighbouring pads.

13. The milking system according to claim 1, wherein the control unit is arranged to control the tape mover to move the tape over such a distance that another of said separator lines is moved into said determined position.

14. The milking system according to claim 13, wherein the control unit is arranged to control the tape mover to move the tape over such a distance that the Nth subsequent separator line, is moved into said determined position, the distance being substantially equal to N times a centre-to-centre distance between lengthwise neighbouring pads, where N=2, 3, . . . .

15. The milking system according to claim 13, wherein the camera is positioned having a field of view that contains a plurality of pads.

16. The milking system according to claim 13, wherein the reagent pads are mutually separated by the separator line comprising a set of at least two mutually parallel laser ablation lines, and wherein said distance is substantially equal to a centre-to-centre distance between lengthwise neighbouring pads.

17. The milking system according to claim 1, wherein the control unit is arranged to control the tape mover to move the tape over such a distance that the Nth subsequent separator line, is moved into said determined position, the distance being substantially equal to N times a centre-to-centre distance between lengthwise neighbouring pads, where N=2, 3, . . . .

18. The milking system according to claim 17, wherein the camera is positioned having a field of view that contains a plurality of pads.

19. The milking system according to claim 1, wherein the camera is positioned having a field of view that contains a plurality of pads.

20. The milking system according to claim 1, wherein the reagent pads are mutually separated by the separator line comprising a set of at least two mutually parallel laser ablation lines, and wherein said distance is substantially equal to a centre-to-centre distance between lengthwise neighbouring pads.

* * * * *